US012064097B2

(12) United States Patent
Ackroyd

(10) Patent No.: US 12,064,097 B2
(45) Date of Patent: *Aug. 20, 2024

(54) DUAL NEEDLE CORE BIOPSY INSTRUMENT

(71) Applicant: Robert K Ackroyd, Windham, ME (US)

(72) Inventor: Robert K Ackroyd, Windham, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/173,896

(22) Filed: Feb. 24, 2023

(65) Prior Publication Data

US 2023/0190245 A1 Jun. 22, 2023

Related U.S. Application Data

(63) Continuation of application No. 14/850,994, filed on Sep. 11, 2015, now Pat. No. 11,589,846.

(60) Provisional application No. 62/049,783, filed on Sep. 12, 2014.

(51) Int. Cl.
*A61B 10/02* (2006.01)

(52) U.S. Cl.
CPC ........ *A61B 10/0233* (2013.01); *A61B 10/025* (2013.01); *A61B 2010/0208* (2013.01); *A61B 2010/0225* (2013.01)

(58) Field of Classification Search
None
See application file for complete search history.

(56) References Cited

U.S. PATENT DOCUMENTS

| | | | |
|---|---|---|---|
| 4,708,147 A * | 11/1987 | Haaga | A61B 10/0266 600/566 |
| 5,415,182 A | 5/1995 | Chin et al. | |
| 5,842,999 A | 12/1998 | Pruitt et al. | |
| 6,027,458 A | 2/2000 | Janssens | |
| 8,882,681 B2 | 11/2014 | Neoh | |
| 9,968,338 B2 | 5/2018 | Shabaz | |
| 2001/0001059 A1* | 5/2001 | Love | A61B 10/0045 435/7.1 |
| 2002/0007130 A1* | 1/2002 | Burbank | A61B 18/12 600/564 |
| 2002/0026188 A1 | 2/2002 | Balbierz et al. | |
| 2006/0089564 A1* | 4/2006 | Goldenberg | A61B 10/0233 600/566 |
| 2008/0114265 A1 | 5/2008 | Tarter et al. | |
| 2008/0300506 A1 | 12/2008 | McIntyre | |
| 2009/0187118 A1 | 7/2009 | Kim et al. | |
| 2012/0022397 A1 | 1/2012 | Jarial | |
| 2013/0006143 A1 | 1/2013 | Neoh | |
| 2014/0228661 A1 | 8/2014 | Popa-Simil et al. | |
| 2014/0276051 A1* | 9/2014 | Hoffman | A61B 17/3417 604/164.09 |
| 2014/0276202 A1 | 9/2014 | Polster et al. | |
| 2014/0323910 A1 | 10/2014 | Lee | |

(Continued)

*Primary Examiner* — Benjamin S Melhus
(74) *Attorney, Agent, or Firm* — Tredecim LLC; Sean L. Sweeney

(57) ABSTRACT

The embodiments presented herein present a single needle core biopsy instrument and modification required that convert the single needle core biopsy instrument to a dual needle core biopsy instrument. Depending on the design, the dual needle core biopsy instrument includes a dual cannula component that facilitates the simultaneous extraction of tissue or bone specimens.

6 Claims, 9 Drawing Sheets

(56) References Cited

U.S. PATENT DOCUMENTS

2015/0045665 A1   2/2015   Lau
2015/0112248 A1*  4/2015   Helliwell ............ A61M 5/3134
                                                          604/32

* cited by examiner

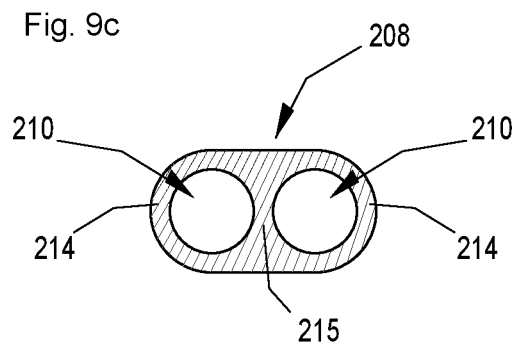
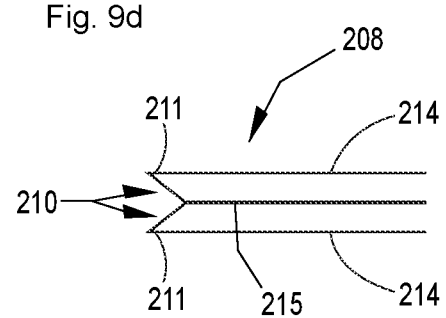

DUAL NEEDLE CORE BIOPSY INSTRUMENT

CROSS-REFERENCE TO RELATED APPLICATIONS

This application is a continuation of U.S. application Ser. No. 14/850,994 filed Sep. 11, 2016, which claims the benefit of U.S. Provisional Patent Application No. 62/049,783 filed Sep. 12, 2014. Each of these prior applications are incorporated herein by reference in their entirety for all purposes.

BACKGROUND

The era of Molecular diagnostics and personalized medicine is now upon us and it will continue to rapidly grow into the next decade. Novel techniques for the diagnosis and treatment of Cancer and other diseases are evolving in an exponential basis as the genetic code of disease is dissected from tissue and blood samples.

As more and more molecular markers are discovered, we are able to subdivide all cancer types into different genetic subtypes. We are discovering that many morphologically identical tumors responded differently to the same treatment regimens. When many of these tumors are compared genetically, there are sometimes specific differences that would predict which patients would respond well to a particular treatment while also predicting which patients will not respond. Treatments destined to fail impart increased morbidity, unnecessary side effects, and leave the patient more compromised and still in need of an alternate treatment protocol. Ineffective treatment also wastes both medical resources and dollars. By identifying the genetic subtypes of many cancers, patients can be treated with the most appropriate protocols.

The realization of personalized medicine is upon us as more and more cancers can be classified on their genetic signatures. These subtypes can be targeted with tailored treatments that more effectively can combat the cancer and significantly reduce the overall side effects.

There are many techniques that can test for the different genetic subtypes of cancers and the most reliable material to use in many tests is an actual sample of fresh tumor. Needle core biopsies are usually the first choice in acquiring tissue for diagnosis. They are minimally invasive, require little if any recovery time, and provide diagnostic tissue for pathologic evaluation. Core biopsies are small and needed for pathologic diagnosis. If additional core biopsies are available for molecular studies, there is no guarantee that each individual core will have diagnostic tissue present. This presents the possibility of false negative molecular results.

Genetic subtypes of tumors can be best evaluated with tissue samples. Needle core biopsies are suitable for these tests, however, without microscopic confirmation, it is impossible to guarantee that the sample taken for genetic testing adequately represents the tumor being biopsied. Multiple core biopsies could be taken from a tumor, but there can often be some variation in the location sampled. Some cores may or may not have any tumor. It would be preferable that the tissue being sent for molecular testing was confirmed (microscopically) to truly have tumor cells present.

SUMMARY OF THE INVENTION

The present invention solves the problems associated with taking multiple samples simultaneously. Specifically, the present invention enables the collection of two samples directly adjacent to each other at exactly the same time, thereby ensuring that the two samples of the tissue taken for biopsy would be representative of each other. The first of these samples could be sent for microscopic diagnostic evaluation and the second could be submitted for genetic or other specialized studies. The present invention also ensures that only diagnostic tissue would be sent for the more expensive molecular or other specialized testing because if the tumor tissue was not represented by microscopy, the molecular test would not be processed.

The present invention is directed to a dual cannula component for use in a dual needle core biopsy instrument. The dual cannula component comprises dual canula cylinders, the dual cannula cylinders being a contiguous member having a pair of substantially parallel bores. The bores extend the length of the dual cannula cylinders to create a first cannula having a lumen and a tip at a distal end thereof and a second cannula having a lumen and a tip at a distal end thereof. The first cannula lumen is separated from the second cannula lumen by a central portion, the central portion being a shared wall of the first cannula and the second cannula.

BRIEF DESCRIPTION OF THE DRAWINGS

These and other features, aspects and advantages of the present invention will become better understood with reference to the following description, appended claims, and accompanying drawings where:

FIG. 9c illustrates a sectional view of a portion of the dual canula component.

FIG. 9d illustrates a top view of a portion of the dual cannula component.

DETAILED DESCRIPTION OF THE INVENTION

The detailed description will first present the design and use of a single needle core biopsy instrument 100. It will then modify this design to illustrate how a dual needle core biopsy instrument 200 may be obtained by modifying the single needle core biopsy instrument design.

Figure 1:
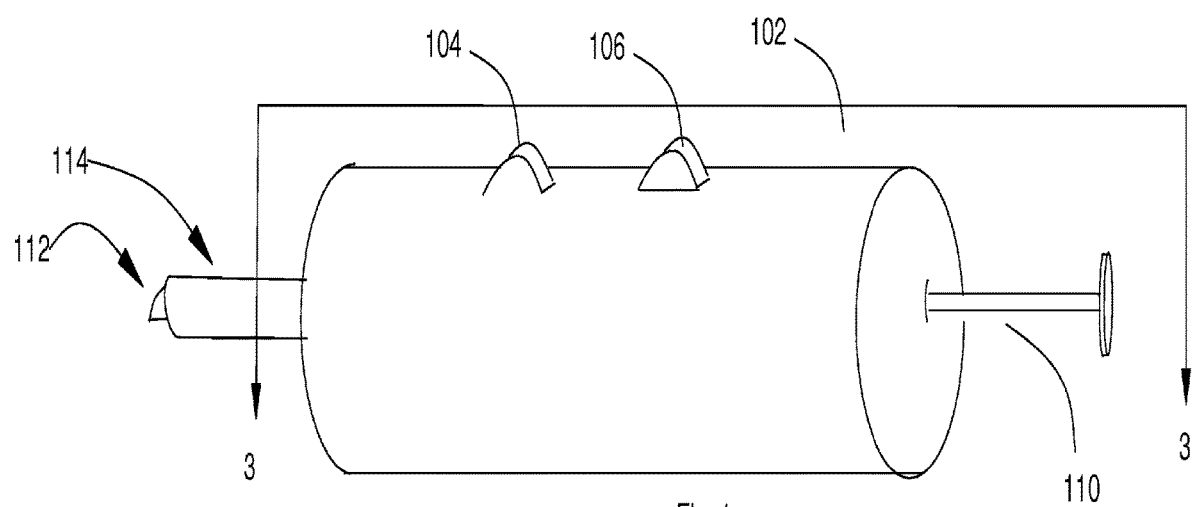
FIG. 1 is a front perspective view of a single needle core biopsy instrument.

FIG. 1 is a front perspective view of a single needle core biopsy instrument 100. Illustrated in FIG. 1 is a case 102, a first sliding button 104, a second sliding button 106, a cannula cylinder 114, a plunger 110, and the needle 112. In the following, the term forward means towards the needle 112 end and the term backward means towards the plunger 110 end. Similarly, the terms clockwise and counterclockwise refer to the figure under discussion.

Figure 2A:
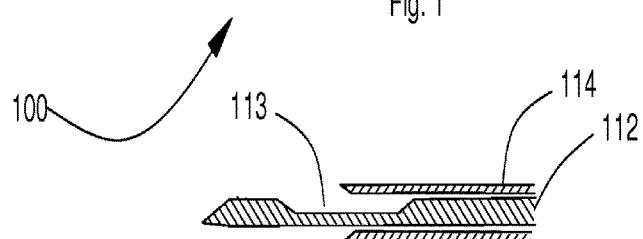
FIGS. 2a and 2b illustrate sectional view of a portion of the needle and the cannula cylinder with the needle in a retracted and extended position respectively.
Figure 2B:
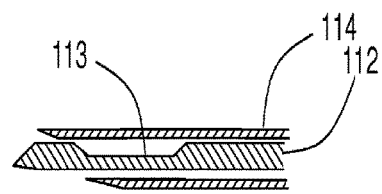

FIGS. 2a and 2b illustrate sectional views of a portion of the needle 112 and the cannula cylinder 114 with the needle 112 in an extended and retracted position respectively. The needle 112 has a tissue receiving recess 113 that collects the tissue material during the biopsy collection process.

Figure 3:
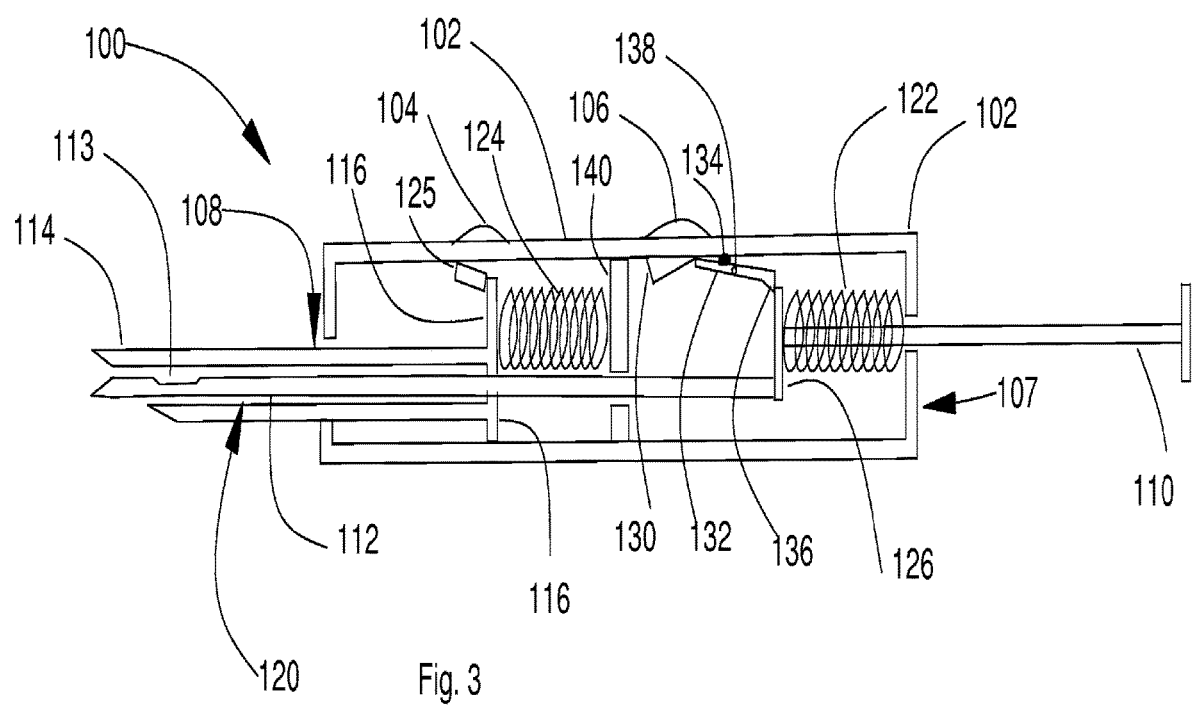
FIG. 3 is a sectional view of the needle core biopsy instrument.

FIG. 3 is a sectional view of the needle core biopsy instrument, the section indicated in FIG. 1. It has a case component 107, a cannula component 108, a needle component 120, and a trigger component 128. The case component 107 has a case 102 and a case barrier 140. The case has a cylindrical shape and the case barrier has the shape of a cylindrical disk imbedded within the case with its disk sides perpendicular to the longitudinal axis of the case cylinder. Both the case and case cylinder have holes that facilitate the movements of the needle and the cannula cylinder.

Referring again to FIG. 3, the cannula component 108 is comprised of a cannula cylinder 114 and a cannula cylindrical back 116. The cannula cylinder 114 is attached to the cannula cylindrical back 116 and is slidingly mounted in case 102. Also included in the cannula component 108 is first sliding button 104 mounted on the case 102. The first sliding button 104 can slide the cannula component 108 forward towards the needle end of the biopsy instrument and backwards towards the plunger end of the biopsy instrument. It also has a lock that can lock the cannula component 108 in place. The cannula spring 124 sits between the case barrier 140 and the cannula cylindrical back 116. A lever 125 engages the first sliding button.

Referring again to FIG. 3, the trigger component 128 is comprised of a second sliding button 106, a wedge 130, a swivel 132 rotationally mounted on case 102, and a swivel spring 134 The needle component 120 is comprised of a needle 112, a plunger spring 122, the plunger 110, and needle cylindrical back 126.

Figure 4:
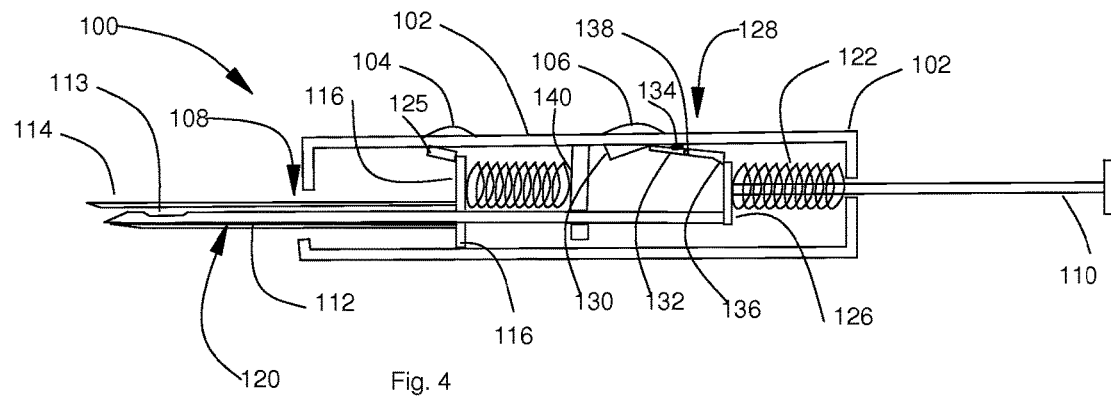
FIGS. 4 through 8 illustrate the five steps of using the single needle core biopsy instrument in obtaining a biopsy tissue sample.

FIGS. 4 through 8 illustrate the use of the single needle core biopsy instrument 100 in obtaining a biopsy tissue sample, Step 1. Cocking the single needle core biopsy instrument 100 ready for firing:

Referring to FIG. 4, the first sliding button 104 is pushed forward and locked, holding the cannula component 108 in a forward position. The plunger 110 is pulled towards the backward direction, compressing the plunger spring 122. The second sliding button 106 is pushed in a forward direction. This causes the wedge 130 to disengage with the swivel 132. The swivel spring 134 then forces the swivel 132 to rotate around the swivel pin 138 in a clockwise direction, forcing the swivel tip 136 downward engaging the needle cylindrical back 126. The single needle core biopsy instrument 100 is then cocked, ready for firing.

Figure 5:
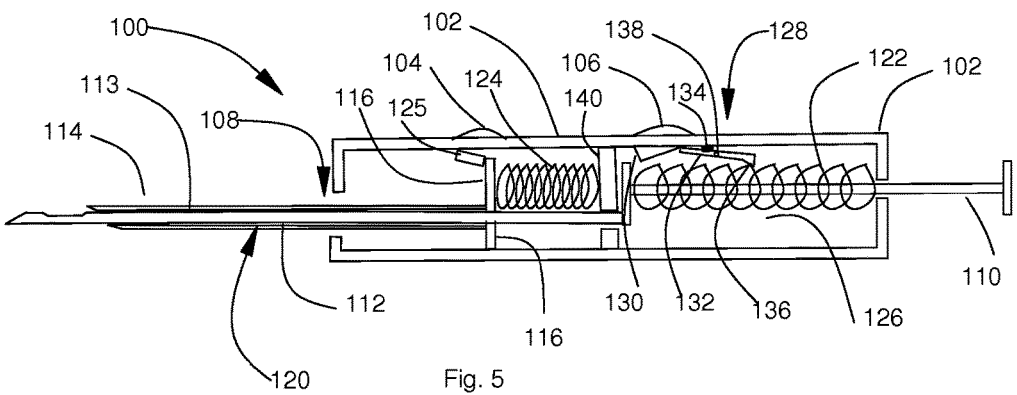

Step 2. Firing the single needle core biopsy instrument 100:

Referring to FIG. 5, the user positions the needle 112 at the patient's body part ready for the biopsy sample to be taken. The second sliding button 106 is pushed backward, forcing the wedge 130 backward, causing the swivel 132 to rotate counterclockwise, thereby raising the swivel tip 136, and disengaging from the needle cylindrical back 126. This causes the plunger spring 122 to fire the needle 112 forward. The needle 112 is then thrusted towards the patient's body, penetrates the body and collects a tissue specimen in the tissue receiving recess 113.

Figure 6:
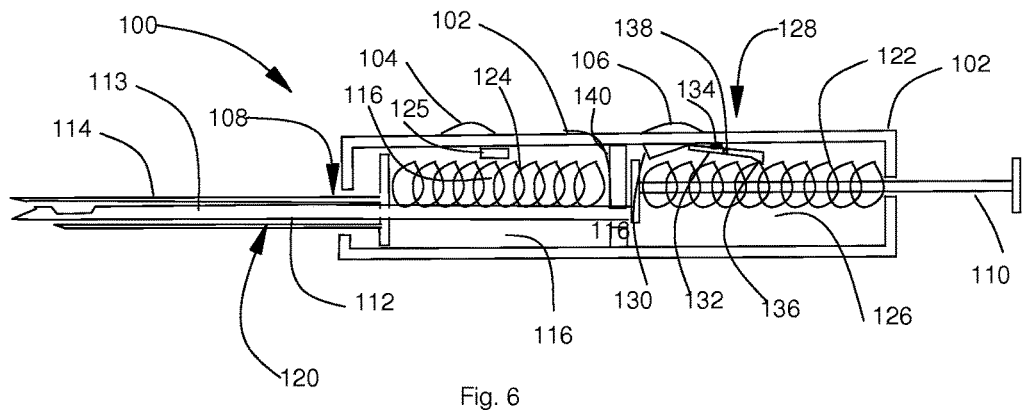
Figure 7:
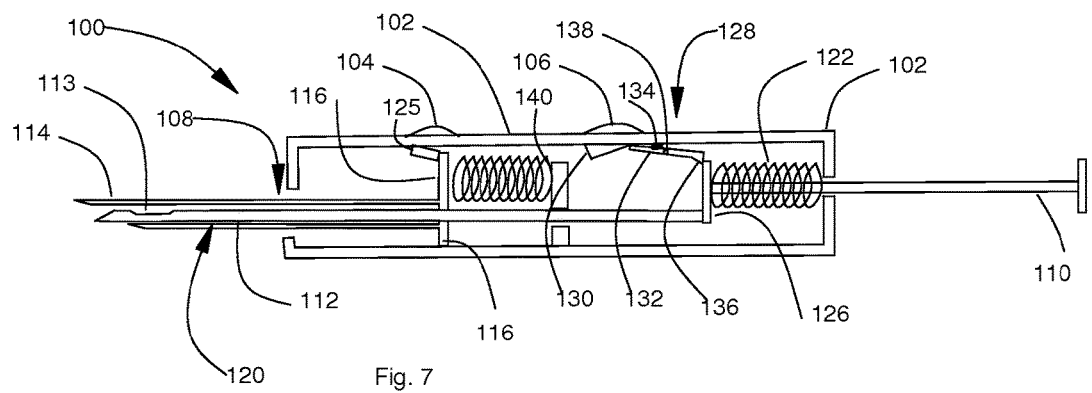

Step 3. Firing the dual needle cannula component:

Referring to FIG. 6, once the plunger spring 122 fires the needle 112 forward (Step 2), the user presses the first sliding button 104, causing the lever 125 to release the cannula spring 124, thereby firing the cannula component 108. This cause the cannula cylinder 114 to thrust forward, enclosing the needle tip and capturing the tissue collected in the tissue receiving recess 113.

Step 4. Withdrawing the needle:

First, the needle 112 enclosing the tip of the cannula cylinder 114 is removed from the patient. Then, referring to FIG. 7, the plunger 110 is pulled backward, and the second sliding button 106 is pushed forward. This causes the needle component 120 to move backward, and the swivel 132 to rotates clockwise until the swivel 132 tip engages the needle cylindrical back 126, keeping the instrument in a cocked position. The biopsy sample is contained in the tissue receiving recess 113.

Figure 8:
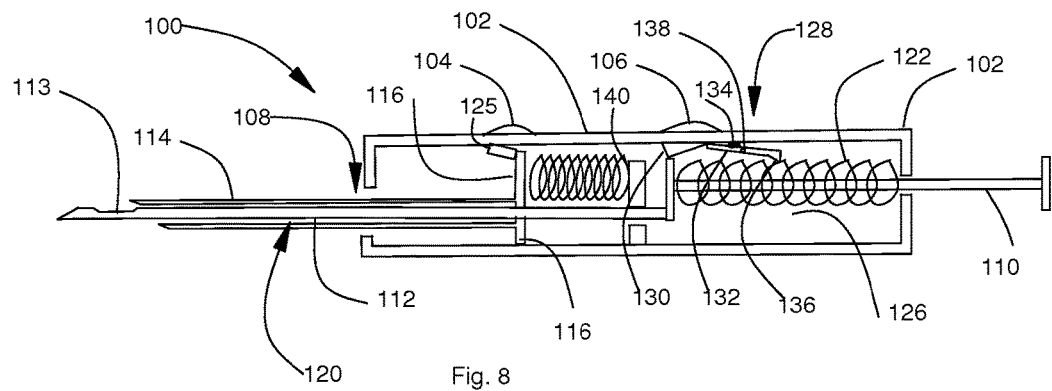

Step 5. Extracting the Biopsy Tissue Sample:

Referring to FIG. 8, to extract the biopsy tissue specimen, the first sliding button 104 is pushed backward, moving the cannula component 108 backward. This exposes the tissue receiving recess 113 containing the biopsy tissue specimen, which may then be removed by the user.

Figure 9:
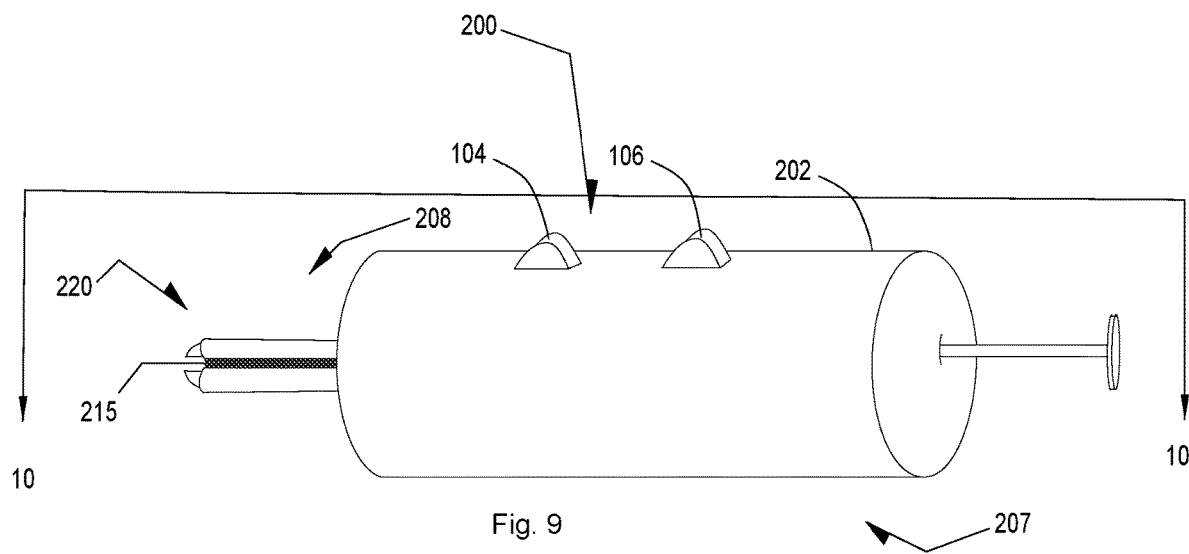
FIG. 9 illustrates a front perspective view of the dual needle core biopsy instrument.

The dual needle core biopsy instrument 200 is a modification of the single needle core biopsy instrument 100. FIG. 9 illustrates a front perspective view of the dual needle core biopsy instrument 200. In the following discussion the numerals used in the single needle core biopsy instrument 100 will be used for the dual needle core biopsy instrument 200 where the parts are essentially unchanged. New numerals will be used for the dual needle core biopsy instrument 200 when the parts are modified.

Referring to FIG. 9, the dual needle core biopsy instrument 200 is comprised of a dual needle case 202, a first sliding button 104, a second sliding button 106, dual cannula cylinders 214, a plunger 110, and dual needles 212. Similar to the description for the single needle core biopsy instrument 100 the term forward means towards the dual needles 212 end and the term backward means towards the plunger end.

Figure 9A:
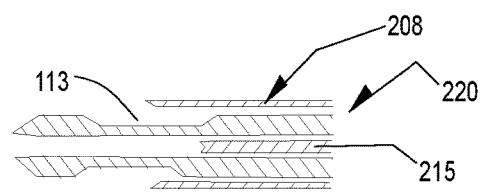
FIGS. 9a and 9b illustrate sectional views of a portion of the dual needle and the dual needle cannula cylinders with the dual needles in a retracted and extended position respectively.
Figure 9B:
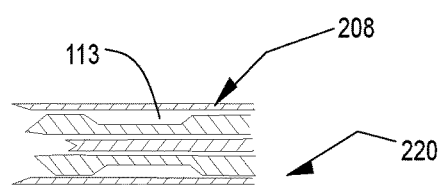

FIGS. 9a and 9b illustrate sectional views of a portion of the dual needle 212 and the dual cannula cylinders 214 with the dual needles 212 in an extended and retracted position respectively. Note that the dual needles 212 each has a tissue receiving recess 113 that collects the tissue material during the biopsy collection process.

Figure 10:
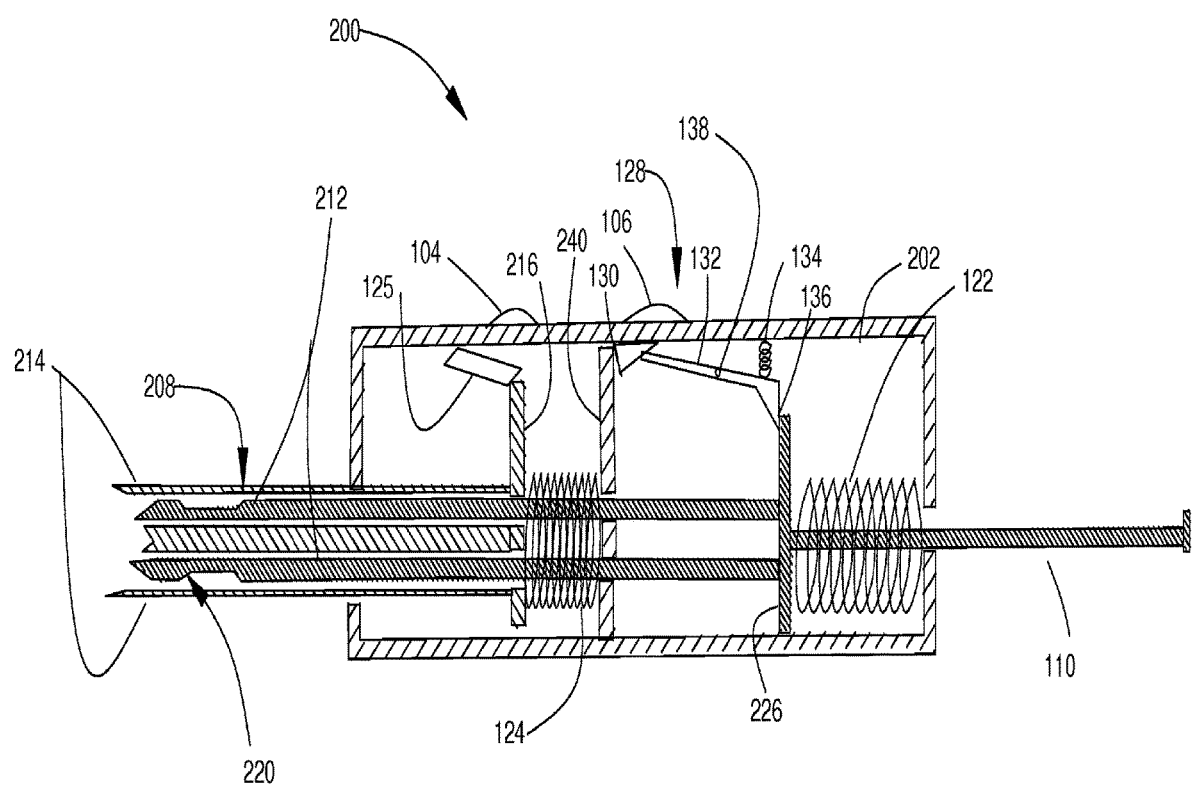
FIG. 10 is a sectional view of the dual needle core biopsy instrument.

FIG. 10 is a sectional view of the dual needle core biopsy instrument 200, the section indicated in FIG. 9. It has a dual needle case component 207, a dual cannula component 208, a dual needle component 220, and a trigger component 128.

Referring to FIG. 10, the dual needle case component 207 has a dual needle case 202 and a dual needle case barrier 240. The dual needle case 202 has a cylindrical shape and the dual needle case barrier 240 has the shape of a cylindrical disk imbedded within the case with its disk parallel sides perpendicular to the longitudinal axis of the case cylinder. Both the dual needle case 202 and dual needle case barrier 240 have holes that facilitate the movements of the dual needles and the dual needle cannula cylinders.

Referring to FIGS. 9, 9a, 9b, 9c, 9d and 10, the dual cannula component 208 is comprised of dual cannula cylinders 214, a central portion 215 and a dual needle cannula cylindrical back 216. The dual cannula cylinders 214 being a contiguous member having a pair of substantially parallel bores, the bores extending the length of the dual cannula cylinders 214 to create a first cannula and a second cannula.

The central portion 215 separates the lumens 210 of the first cannula and the second cannula, resulting in a configuration with a shape analogous to a shotgun barrel, wherein the distal ends of the dual cannula cylinders 214 are substantially aligned and the lumens 210 of the dual cannula cylinders 214 are substantially parallel to each other. The distance between the dual cannula cylinders 214 is determined by the width of the central portion 215. Accordingly, the width of the central portion 215 may be adapted to achieve the desired separation of the dual needles 212, which is preferably between 0.1 mm and 3 mm apart.

The dual cannula cylinders 214 may be angled at their distal ends to form tips 211. As best shown in FIGS. 9 and 9d, the tips 211 may extend from the central portion 215 at an angle such that the tips 211 extend beyond the central portion 215. The dual needle cannula cylindrical back 216 is attached to the dual cannula cylinders 214 at the proximal end of the dual cannula cylinders 214 and the dual cannula component 208 is slidingly mounted in the dual needle case 202. Further, the dual cannula component 208 is attached to first sliding button 104, which is mounted on the dual needle case 202. The first sliding button 104 can slide the dual cannula component 208 forward towards the needle end of the biopsy instrument and backwards towards the plunger end of the biopsy instrument. It also can lock the dual cannula component 208 in place.

Referring again to FIG. 10, the trigger component 128 is comprised of a second sliding button 106, a wedge 130, a swivel 132 rotationally mounted on case 102, and a swivel spring 134. The needle component 120 is comprised of a needle 112, a plunger spring 122, the plunger 110, and dual needle cylindrical back 226.

FIGS. 11 through 14 illustrate the use of the dual needle core biopsy instrument 200 for simultaneously obtaining two biopsy tissue samples. This five step process is analogous to the five step process of the single needle core biopsy instrument 100.

Figure 11:
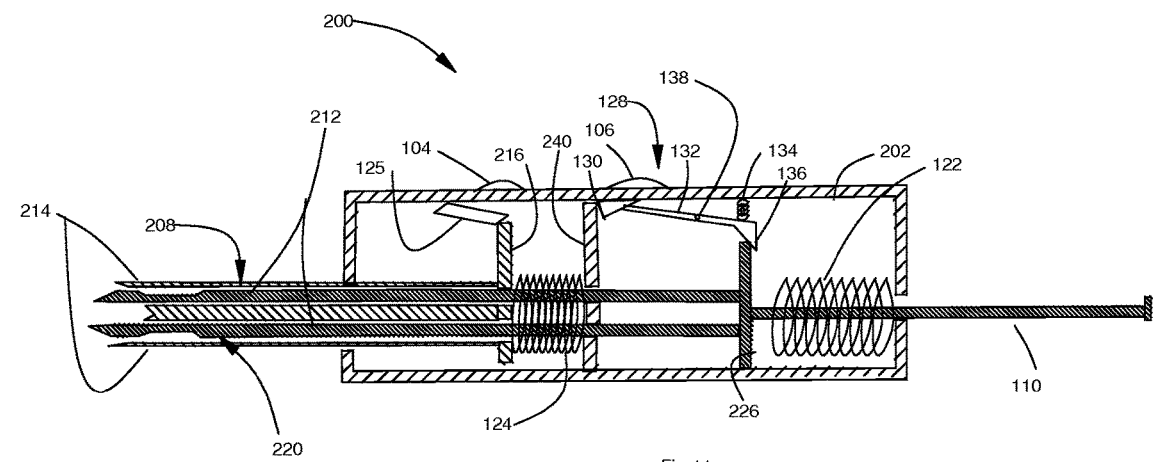
FIGS. 11 through 15 illustrate the five steps of using the dual needle core biopsy instrument in simultaneously obtaining two biopsy tissue samples.

Step 1. Cocking the dual needle core biopsy instrument 200 ready for firing:

Referring to FIG. 11, the first sliding button 104 is pushed forward and locked, holding the dual cannula component 208 in a forward position. The plunger 110 is pulled towards the backward direction, compressing the plunger spring 122. The second sliding button 106 is pushed in a forward direction. This causes the wedge 130 to disengage with the swivel 132. The swivel spring 134 then forces the swivel 132 to rotate around the swivel pin 138 in a clockwise direction, forcing the swivel tip 136 downward engaging the needle dual cylindrical back 226. The dual needle core biopsy instrument 200 is then cocked, ready for firing.

Figure 12:
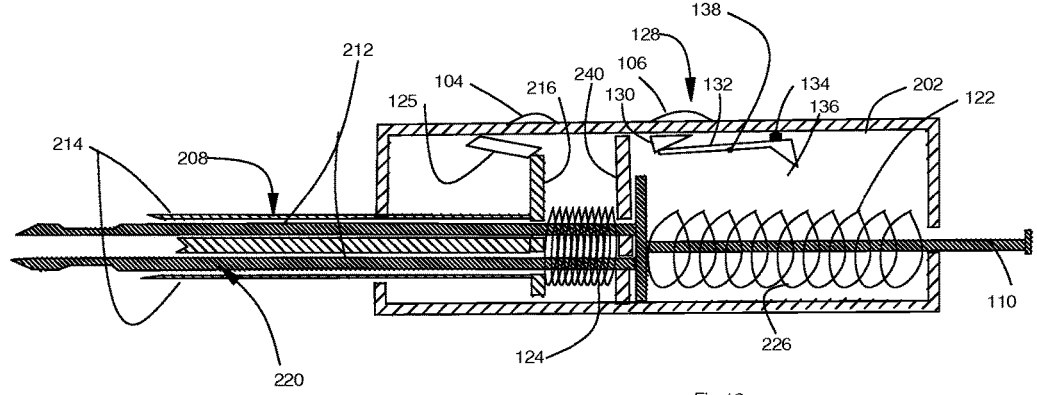

Step 2. Firing the dual needle core biopsy instrument 200:

Referring to FIG. 12, the user positions the dual needles 212 at the patient's body part ready for the dual biopsy samples to be taken. The second sliding button 106 is pushed backward, forcing the wedge 130 backward, causing the swivel 132 to rotate counterclockwise, thereby raising the swivel tip 136, and disengaging from the dual needle cylindrical back 226. This causes the plunger spring 122 to fire the dual needles 212 forward. The dual needles 212 therefore enters the patient's body part, and penetrates the biopsy body tissue, collecting two tissue specimens in the two tissue receiving recesses 213.

Figure 13:
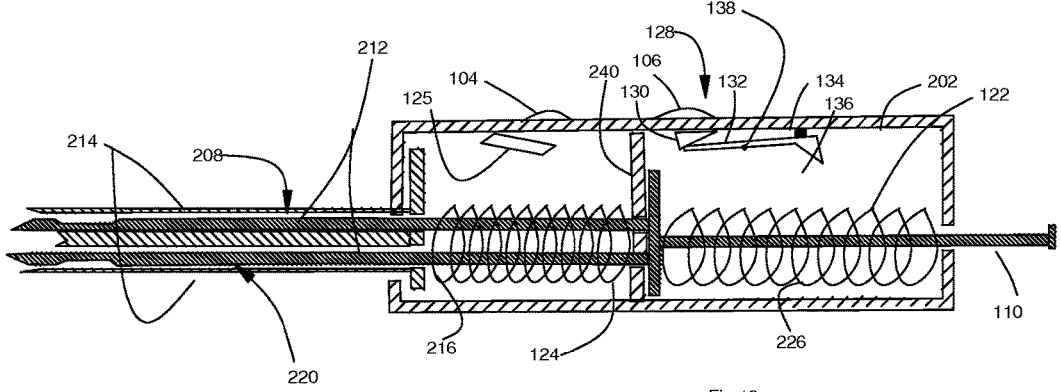

Step 3. Firing the dual needle cannula component:

Referring to FIG. 13, once the plunger spring 122 fires the dual needle component 220 forward (Step 2), the user presses the first sliding button 104, causing the lever 125 to release the cannula spring 124, thereby firing the dual cannula component 208. This cause the dual cannula cylinders 214 to thrust forward, enclosing the dual needle tips and capturing the tissue collected in the two tissue receiving recesses 113.

Figure 14:
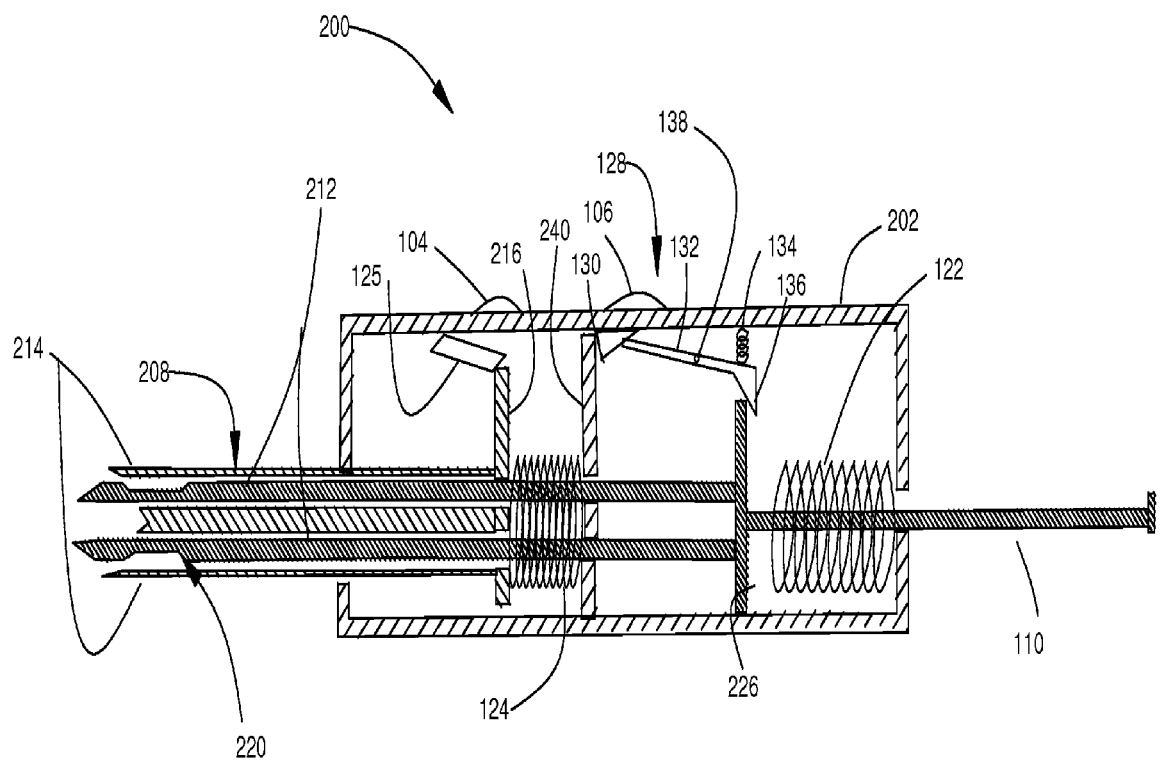
Figure 15:
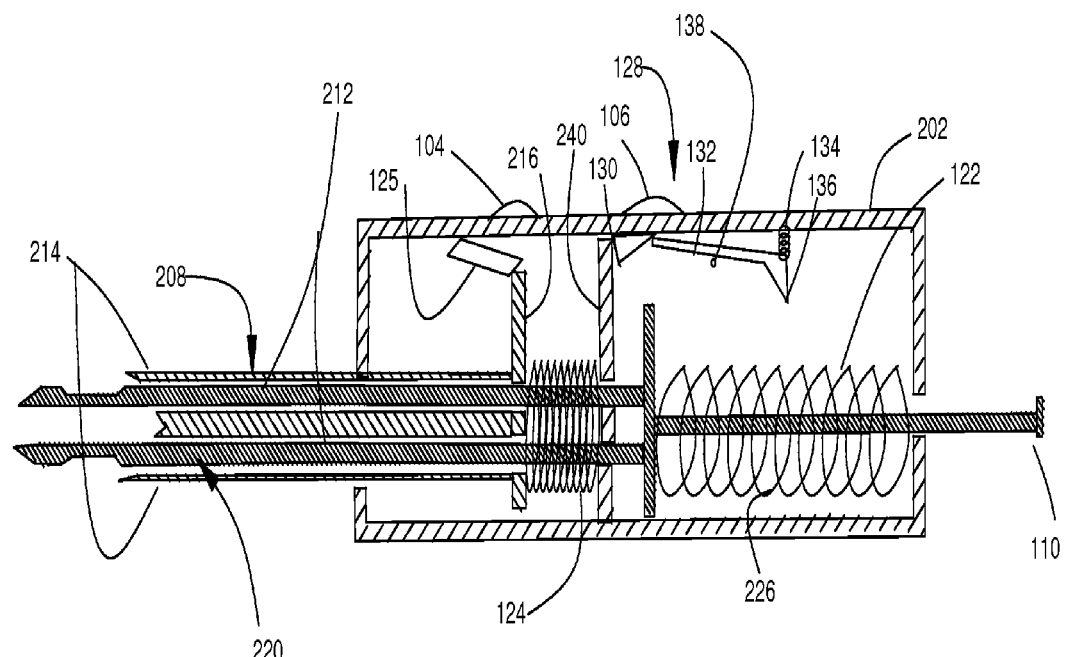

Step 4. Withdrawing the needle:

Referring to FIG. 14, the plunger 110 is pulled backward, and the second sliding button 106 is pushed forward. This causes the dual needle components 220 to move backward, and the swivel 132 to rotate clockwise until the swivel 132 tip engages the dual needle cylindrical back 226, keeping the instrument in a cocked position, Step 5. Extracting the Biopsy Tissue Sample:

Referring to FIG. 15, to extract the two biopsy tissue specimens, the first sliding button 104 is pushed backward, moving the dual cannula components 208 backward. This exposes the two tissue receiving recesses 213 containing the two biopsy tissue specimens, which may then be removed by the user.

The dual needles 212 in the dual needle core biopsy instrument 200 will each have length and diameter similar to the single needle biopsy instrument used for the same application. The distance between the needles will be typically between 0.1 mm and 3 mm apart.

The two embodiments presented above are simple biopsy instrument designs apply to collecting tissue samples. Other embodiments are consistent with the inventive concept presented herein. Almost any single needle core biopsy instrument may be adapted to handle the dual needle concept. The examples presented above apply to tissue specimens. Other designs can apply to taking bone specimens.

The disclosure presented herein gives embodiments of the invention. These embodiments are to be considered only as illustrative of the invention and not a limitation of the scope of the invention. Various permutations, combinations, variations and extensions of these embodiments are considered to fall within the scope of this invention. Therefore the scope of this invention should be determined with reference to the claims and not just by the embodiments presented herein.

What is claimed is:

1. A dual cannula component for use in a dual needle core biopsy instrument, the dual cannula component comprising:
    dual canula cylinders, the dual cannula cylinders being a contiguous member having a pair of substantially parallel bores, the bores extending the length of the dual cannula cylinders to create a first cannula having a lumen and a tip at a distal end thereof and a second cannula having a lumen and a tip at a distal end thereof, the first cannula lumen separated from the second cannula lumen by a central portion, the central portion being a shared wall of the first cannula and the second cannula; and
    a dual needle component comprising a first biopsy needle and a second biopsy needle, the first biopsy needle having a tip and a receiving recess and positioned inside the dual cannula cylinders such that the receiving recess of the first biopsy needle is enclosed within the first cannula lumen, and the second biopsy needle having a tip and a receiving recess and positioned inside the dual cannula cylinders such that the receiving recess of the second biopsy needle is enclosed within the second cannula lumen.

2. The dual cannula component of claim 1, wherein the first biopsy needle and the second biopsy needle are positioned between 0.1 mm and 3.0 mm apart.

3. The dual cannula component of claim 1, further comprising a dual needle cannula cylindrical back, wherein the dual canula cylinders are attached to the dual needle cannula cylindrical back.

4. The dual needle core biopsy instrument of claim 1, wherein the first biopsy needle is positioned within the first cannula lumen such that the first biopsy needle receiving recess is oriented away from the central portion.

5. The dual needle core biopsy instrument of claim 4, wherein the second biopsy needle is positioned within the second cannula lumen such that the second biopsy needle receiving recess is oriented away from the central portion.

6. The dual needle core biopsy instrument of claim 1, wherein the first and second biopsy needles are each positioned within the dual cannula cylinders such that the first biopsy needle receiving recess is oriented away from the second biopsy needle receiving recess.

\* \* \* \* \*